United States Patent
Cong et al.

(10) Patent No.: US 10,713,802 B2
(45) Date of Patent: Jul. 14, 2020

(54) ULTRASONIC IMAGE PROCESSING SYSTEM AND METHOD AND DEVICE THEREOF, ULTRASONIC DIAGNOSTIC DEVICE

(71) Applicant: SHENZHEN MINDRAY BIO-MEDICAL ELECTRONICS CO., LTD., Shenzhen (CN)

(72) Inventors: Longfei Cong, Shenzhen (CN); Teng Sun, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 155 days.

(21) Appl. No.: 15/889,951

(22) Filed: Feb. 6, 2018

(65) Prior Publication Data
US 2018/0300890 A1 Oct. 18, 2018

Related U.S. Application Data

(63) Continuation of application No. PCT/CN2015/086158, filed on Aug. 5, 2015.

(51) Int. Cl.
*G06K 9/00* (2006.01)
*G06T 7/38* (2017.01)
(Continued)

(52) U.S. Cl.
CPC .............. *G06T 7/38* (2017.01); *A61B 8/14* (2013.01); *A61B 8/463* (2013.01); *A61B 8/466* (2013.01);
(Continued)

(58) Field of Classification Search
None
See application file for complete search history.

(56) References Cited

U.S. PATENT DOCUMENTS 7,840,050 B2 * 11/2010 Ramamurthy ........ G06T 7/0012
382/131
9,761,005 B2 * 9/2017 Tahmasebi Maraghoosh ............
G06T 17/20
(Continued)

FOREIGN PATENT DOCUMENTS

CN 101026998 A 8/2007
CN 101273382 A 9/2008
(Continued)

*Primary Examiner* — Soo Jin Park
(74) *Attorney, Agent, or Firm* — Kory D. Christensen

(57) ABSTRACT

An ultrasonic image processing system comprising: a data receiving module for acquiring multiple sets of three-dimensional image data corresponding to a single target tissue; an image analyzing module for dividing, on the basis of any one group of the multiple sets of three-dimensional image data, a target region to obtain a three-dimensional volume structure boundary of the target region, and a safety boundary generated by outward expansion or inward contraction along the three-dimensional volume structure boundary; an image mapping module for establishing a spatial mapping relation between the multiple sets of three-dimensional image data, and according to the spatial mapping relation, mapping the three-dimensional volume structure boundary and the safety boundary of the target region to the other sets of three-dimensional image data; and an image marking module for marking, in a displayed image, corresponding three-dimensional volume structure boundaries and safety boundaries of the target region in the multiple sets of three-dimensional image data, or regions within the three-dimensional volume structure boundaries and safety boundaries. The system is capable of solving the problem in the prior art in which collection, analysis and quantitative display cannot be performed on the ultrasonic images during the treatment process.

18 Claims, 8 Drawing Sheets

(51) Int. Cl.
*A61B 8/08* (2006.01)
*G06T 7/11* (2017.01)
*G06T 7/12* (2017.01)
*G06T 7/174* (2017.01)
*A61B 8/14* (2006.01)
*A61B 8/00* (2006.01)
*G06T 11/00* (2006.01)

(52) U.S. Cl.
CPC ............ *A61B 8/468* (2013.01); *A61B 8/469* (2013.01); *A61B 8/483* (2013.01); *A61B 8/5215* (2013.01); *A61B 8/5246* (2013.01); *G06T 7/11* (2017.01); *G06T 7/12* (2017.01); *G06T 7/174* (2017.01); *G06T 11/003* (2013.01); *G06T 2200/04* (2013.01); *G06T 2207/10136* (2013.01); *G06T 2207/20112* (2013.01); *G06T 2207/20221* (2013.01); *G06T 2207/30096* (2013.01)

(56) References Cited

U.S. PATENT DOCUMENTS

| | | | |
|---|---|---|---|
| 9,934,579 B2* | 4/2018 | Prevost | G06T 7/149 |
| 10,290,076 B2* | 5/2019 | Kadoury | G06T 11/008 |
| 2011/0178389 A1* | 7/2011 | Kumar | A61B 5/055 |
| | | | 600/411 |
| 2012/0035464 A1* | 2/2012 | Raju | A61N 7/02 |
| | | | 600/411 |
| 2014/0073910 A1 | 3/2014 | Munrow et al. | |

FOREIGN PATENT DOCUMENTS

| | | |
|---|---|---|
| CN | 101964118 A | 2/2011 |
| CN | 102999902 A | 3/2013 |
| CN | 103077550 A | 5/2013 |

\* cited by examiner

ULTRASONIC IMAGE PROCESSING SYSTEM AND METHOD AND DEVICE THEREOF, ULTRASONIC DIAGNOSTIC DEVICE

TECHNICAL FIELD

The present disclosure relates to ultrasonic image processing and more particularly to an ultrasonic image processing system and method and device thereof

BACKGROUND

Currently, there are three kinds of ultrasound interventional ablation methods used for the treatment of a cancer: radiofrequency ablation (RFA), cryoablation, and microwave ablation. In these three methods, a special needle or ablation probe is placed to a location of a tumor (inserted into the tumor) through the skin or body lumen structure of a human By local heating (for the radiofrequency ablation and the microwave ablation) or freezing (for the cryoablation), the tumor cells can be killed. Ultrasound imaging is applied throughout the procedure of the interventional ablation. With the ultrasound waves, a great deal of image information can be obtained relating to the disease organization during the diagnosis, preoperative, and postoperative stages. In this way, important complementary physiological and anatomical information can be provided for the research, treatment, and diagnosis of disease.

Take tumor treatment as an example. Generally a tumor is approximately spherical, while the ablated area obtained by the radiofrequency ablation or the microwave ablation is ellipsoidal. Therefore, it often occurs clinically that the ablated area completely covers the tumor boundary in the direction of the ablation needle (the long axis direction of the ellipsoidal ablated area) while does not completely cover the tumor boundary in the direction perpendicular to the direction of the ablation needle. In order to address this issue, ultrasound contrast imaging is used to evaluate the results of the interventional treatment.

Currently, the main evaluation method is performing ultrasound two-dimensional contrast imaging before and after the ablation to measure the long diameter of the tumor and the long diameter of the ablated area. However, the consistency between the ultrasound sections and locations in the two measurements cannot be guaranteed. Particularly, when the ablation is performed for multiple times to treat a large tumor, the simple measurement of the long diameter of the ablated area cannot represent the entire ablated area. The current three-dimensional ultrasound contrast imaging is mainly used to separate states of a target area. Alternatively, 4D imaging is used to display the dynamic blood perfusion in a target area. However, neither method can provide a quantitative data reference for ablation effects.

Therefore, there is a need to provide a new ultrasonic image processing system to provide more efficient quantitative data reference for cancer treatment or other medical processes.

SUMMARY

An ultrasound image processing system may include: a data receiving unit which may obtain multiple sets of three-dimensional image data of a same target tissue, where the multiple sets of three-dimensional image data may include at least two sets of three-dimensional image data; an image mapping unit which may obtain a spatial mapping relationship between the multiple sets of three-dimensional image data; an image analysis unit which may segment a target area according to any one group of three-dimensional image data of the multiple sets of three-dimensional image data to obtain a boundary of the target area and map the boundary to other sets of three-dimensional image data according to the spatial mapping relationship; a display processing unit which may display at least one displaying image obtained by reconstructing at least one group of three-dimensional image data of said other sets of three-dimensional image data in a display interface; and an image marking unit which may mark the boundary or an area within the boundary on the displaying image.

An ultrasonic image processing method may include: obtaining multiple sets of three-dimensional image data of a same target tissue, where the multiple sets of three-dimensional image data may include at least two sets of three-dimensional image data; obtaining a spatial mapping relationship between the multiple sets of three-dimensional image data; segmenting a target area according to any one group of three-dimensional image data of the multiple sets of three-dimensional image data to obtain a boundary of the target area and maps the boundary to other sets of three-dimensional image data according to the spatial mapping relationship; displaying at least one displaying image obtained by reconstructing at least one group of three-dimensional image data of said other sets of three-dimensional image data in a display interface; and marking the boundary or an area within the boundary on the displaying image.

An ultrasonic image processing device may include: a storage unit which may store multiple sets of three-dimensional image data of a same target tissue and results of manipulations performed on the multiple sets of three-dimensional image data, where the multiple sets of three-dimensional image data may include at least two sets of three-dimensional image data; a human-machine interaction input device which may obtain manipulation data to the multiple sets of three-dimensional image data; a display device which may display the displaying image obtained by reconstruction of the multiple sets of three-dimensional image data; and a processor which may process the multiple sets of three-dimensional image data based on the obtained manipulation data and output results of the processing, where the processor may: obtain a spatial mapping relationship between the multiple sets of three-dimensional image data; segment a target area according to any one group of three-dimensional image data of the multiple sets of three-dimensional image data to obtain a boundary of the target area, and map the boundary of the target area to other sets of three-dimensional image data according to the spatial mapping relationship; obtain at least one displaying image by reconstruction of at least one group of three-dimensional image data of said other sets of three-dimensional image data and display the at least one displaying image on the display device; and mark the boundary of the target area on the at least one displaying image or mark an area within the boundary on the at least one displaying image.

An an ultrasonic diagnosis device may include an image acquisition unit and the ultrasonic image processing device discussed above. The image acquisition unit may transmit ultrasound waves and receive ultrasound echoes to obtain three-dimensional image data of a target tissue.

The present disclosure provides new solution for quantitatively and comparatively displaying the effects of tumor ablation. In the disclosed image processing systems, methods, and devices, the three-dimensional image data acquired before and after the ablation operation may be comparatively displayed in two or more windows, and the tumor tissue area and the safety boundary may also be comparatively displayed. With the solutions of the present disclosure, the effects of the ablation may be shown by images on-site after the ablation treatment, thereby providing a visible quantitative data reference for the evaluation of the effects of the ablation operation.

DETAILED DESCRIPTION

In the present disclosure, a new ultrasonic image processing system and method and device are disclosed, which have a quantitative comparison function for the effects of tumor ablation. With the solutions of the present disclosure, multiple sets of three-dimensional ultrasonic image data during tumor ablation may be comparatively displayed, and changes of situations (including the shape and size of the tumor and the safety boundary in ablation treatment) of a disease area during the tumor ablation may be intuitively displayed on a display interface, thereby providing more effective and visible quantitative data reference for cancer treatment of other medical processes. The solutions of the present disclosure will be described in detail with reference embodiments below.

Figure 1:
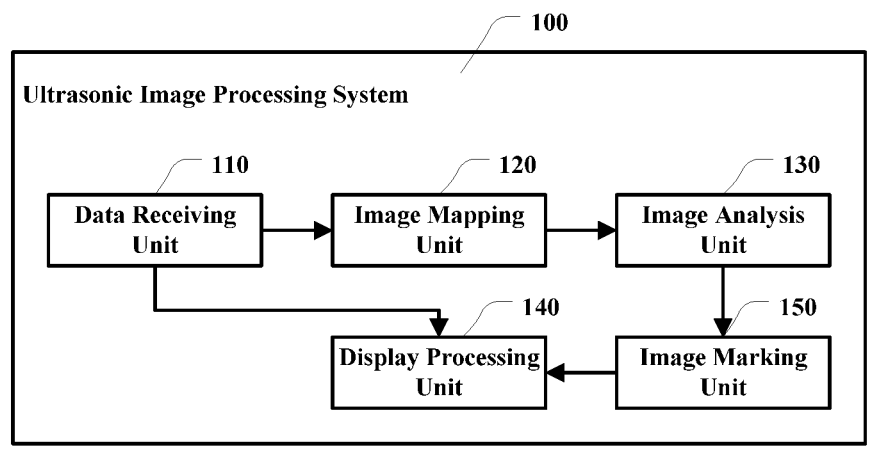
FIG. 1 schematically shows the ultrasonic image processing system in one embodiment.

As shown in FIG. 1, in one embodiment, an ultrasonic image processing system may be provided, which may include:

a data receiving unit 110 which may obtain multiple sets of three-dimensional image data of a same target tissue, where the multiple sets of three-dimensional image data may include at least two sets of three-dimensional image data;

an image mapping unit 120 which may obtain a spatial mapping relationship between the multiple sets of three-dimensional image data;

an image analysis unit 130 which may segment a target area according to any one group of three-dimensional image data of the multiple sets of three-dimensional image data above to obtain a boundary of the target area and map the boundary of the target area to other sets of three-dimensional image data according to the spatial mapping relationship;

a display processing unit 140 which may display, in an display interface, at least one displaying image obtained by reconstruction of at least one of said other sets' three-dimensional image data (i.e. the other sets three-dimensional image data except the one group of three-dimensional image data used to segment the target area to obtain the boundary of the target area); and an image marking unit 150 which may mark the boundary of the target area in the displaying image or marking an area within the boundary of the target area in the displaying image.

In various embodiments, the mentioned "boundary" of the target area may be a structural boundary of three-dimensional volume of the target area, a corresponding boundary obtained by expanding or retracting a predetermined width from the structural boundary of three-dimensional volume (this boundary is referred to as safety boundary) or any other suitable or desired boundary which is objectively existing or defined by the system. In the specific embodiments below, the structural boundary of three-dimensional volume and/or safety boundary will be used as examples. However, the present disclosure will not be limited to the structural boundary of three-dimensional volume and/or the safety boundary.

In various embodiments of the present disclosure, the structural boundary of three-dimensional volume may be a shape boundary of the structure corresponding to the segmented target area in the displaying image, while the safety boundary may be a corresponding boundary obtained by expanding or retracting a predetermined width from the structural boundary of three-dimensional volume. When the image is displayed, the structural boundary of three-dimensional volume and the safety boundary should not be considered as only a circle of single pixels located at locations where the boundary is located in the displaying image, but may further include all pixels located within a predetermined width in the vicinity of the boundary. Accordingly, when marking the structural boundary of the three-dimensional volume and the safety boundary, all pixels located within a predetermined width in the vicinity of the boundaries may be marked.

In the embodiments above, the at least two sets of three-dimensional image data of a same target tissue may be obtained by imaging the target tissue by at least two times. For example, the at least two sets of three-dimensional image data may be multiple three-dimensional image data sets obtained by imaging the target tissue during different stages, such as during various examination stages of the patient, before an ablation operation, after an ablation operation, before a second operation, and/or after a second operation. The three-dimensional image data may be three-dimensional ultrasound tissue image data, three-dimensional ultrasound contrast image data or three-dimensional image data containing both ultrasound tissue image data and three-dimensional ultrasound contrast image data. The safety boundary may be the safety boundary for tumor ablation treatment, which may be defined as the boundary obtained by expanding outward or retracting inward the tumor area by a predetermined width. The predetermined width here may generally be 5 mm The safety boundary may be generated by generating a binary image based on the segmented three-dimensional volume of the tumor and performing morphological dilation on the binary image to expand outward the tumor volume by a certain distance, where the boundary of the three-dimensional volume after the dilation may be the safety boundary.

Alternatively, normal vectors of the points on the boundary may be calculated based on the three-dimensional shape of the tumor area and the boundary may be expanded outward along the normal vectors by a certain distance to obtain the safety boundary. Reconstructing the multiple sets of three-dimensional image data to obtain multiple displaying images may include reconstructing corresponding two-dimensional image in a same section in the three-dimensional image data using multi-planar reconstruction (MPR) technologies, and may further include reconstructing each group of three-dimensional image data to obtain two-dimensional images in multiple sections and three-dimensional images. The segmentation for obtaining the target area may be achieved by segmenting or marking on one displaying image corresponding to the multiple sets of three-dimensional image data obtained by MPR reconstruction on a display device. The segmentation for obtaining the target area may be performed on the image data before the tumor ablation operation.

In various embodiments of the present disclosure, the target area may be tumor tissue to be ablated. In various embodiments, the three-dimensional volumes of the tumor tissue and the safety boundaries in the ultrasound images before and after the ablation treatment for the tumor can be efficiently comparatively displayed. In one embodiment, two sets of three-dimensional image data before and after the ablation obtained by imaging the tumor tissue before and after the ablation may be comparatively displayed, and the segmented target area obtained by segmentation performed on the three-dimensional image data before the ablation may be mapped to the image after the ablation according to the mapping relationship between the three-dimensional images. Compared to performing separately the segmentation on the image after the ablation to obtain the target area, the current situation of the tumor tissue after the ablation can be show more clearly, more accuracy and more visible comparative analysis data can be provided to medical staffs, and the physiological and anatomical information after the tumor ablation treatment may be shown more intuitively.

Figure 2:
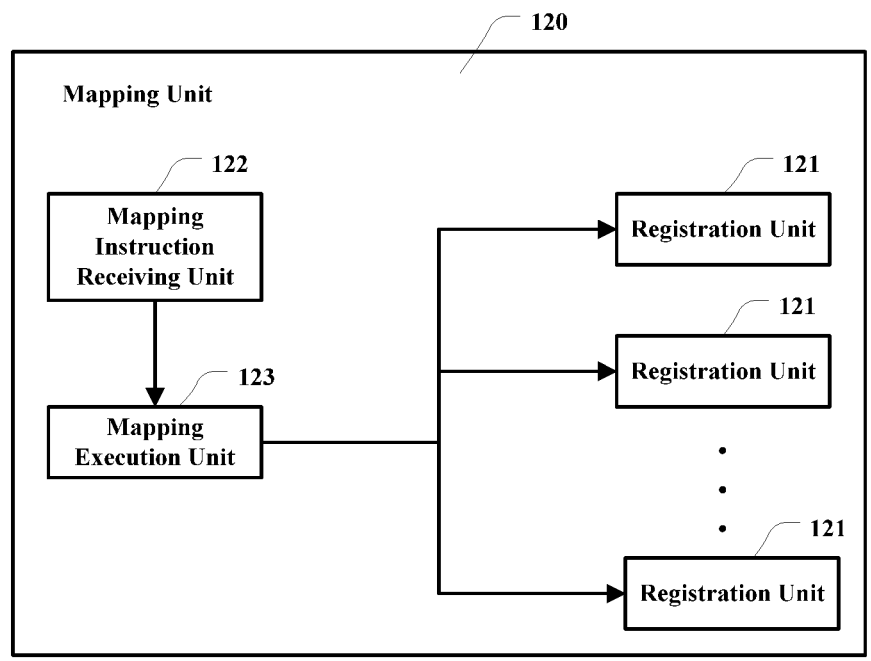
FIG. 2 schematically shows the mapping unit 120 in FIG. 1.

In one embodiment, as shown in FIG. 2, the image mapping unit 120 may include:

at least one registration unit 121 which may obtain the spatial mapping relationship between the multiple sets of three-dimensional image data according to one image registration method;

a mapping instruction receiving unit 122 which may obtain a mapping selection instruction for selecting one or more registration unit through a prompt box, a button, an instruction input box or a gesture displayed on or inputted through the display interface on the display device or a human-machine interaction input device; and a mapping execution unit 123 which may using the registration units selected by the mapping selection instruction to register the multiple sets of three-dimensional image data.

In one embodiment, when the ultrasound contrast imaging is used, the image resulting from fundamental waves (i.e. the tissue image) may be simultaneously obtained with the ultrasound contrast image. The pixels of the contrast image correspond to those of the tissue image. Therefore, the mapping relationship between the contrast image and the tissue image may be obtained without a registration operation. The registration between the images may be performed on the tissue image data, the contrast image data, or both. An automatic registration method between images may include two parts: similarity measurement between images and mapping between images. The mapping methods may include rigid body transformation (rotation and translation) methods, affine transformation (zoom, rotation and translation) methods and nonlinear transformation (using different mapping for different local images) methods. With reference to the characteristics of ultrasound three-dimensional contrast imaging, two types of embodiments using rigid body transformation and affine transformation will be given below. However, the registration methods of the present disclosure will not be limited to a specific registration method described above or below.

In a case that two sets of ultrasound three-dimensional contrast data are collected in the same depth, i.e. the collected pixels have the same scale, the rigid body transformation may be used to register the two images, i.e., the registration may include rotation and translation. In a case that the depths of the two collection are different, an interpolation (e.g. bilinear interpolation, spline interpolation or nearest neighbor interpolation, etc.) may be used to zoom the two sets of three-dimensional image data to a same scale. Thereafter, they may be registered using a rigid body transformation. The registration methods between some images will be described with reference to formulas below.

The registration based on the rigid body transformation may include the following steps.

First, a mapping matrix A may be created to build a spatial mapping relationship function between two sets of three-dimensional ultrasound image, as shown by formula (1) below. Assuming that an intensity of a pixel point $X_i$ of one group of ultrasound three-dimensional contrast image data is $f(X_i)$ and an intensity of a pixel point $Y_i$ of the other group of ultrasound three-dimensional contrast image data is $g(Y_i)$, the mapping between the two sets of ultrasound three-dimensional contrast image data may be represented as:

$$Y_i = AX_i, X_i = \begin{bmatrix} x_1^i \\ x_2^i \\ x_3^i \\ 1 \end{bmatrix}, Y_i = \begin{bmatrix} y_1^i \\ y_2^i \\ y_3^i \\ 1 \end{bmatrix}, A = \begin{bmatrix} a_{11}, & a_{12}, & a_{13}, & T_1 \\ a_{12}, & a_{22}, & a_{23}, & T_2 \\ a_{31}, & a_{32}, & a_{33}, & T_3 \\ 0, & 0, & 0, & 1 \end{bmatrix} \quad \text{formula (1)}$$

Thereafter, a similarity measure function between the two sets of three-dimensional image data may be calculated based on minimum sum of absolute difference (SAD), as shown by formula (2) below.

$$E = \sum_{i=1...N} |f(X_i) - g(AX_i)| \quad \text{formula (2)}$$

In the step above, the similarity measure function between the two sets of three-dimensional image data may also be calculated based on minimum sum of squared difference (SSD) method, maximum cross-correlation (C-C) method or minimum absolute difference method improved based on Rayleigh distribution characteristics of ultrasonic noise. Furthermore, the intensity functions $f(X_i)$ and $g(Y_i)$ in the similarity measure function may be replaced by local gradient, local gray quotient or the like of the corresponding three-dimensional image data.

Thereafter, the formula (1) may be solved based on the results of the similarity measure function to obtain the mapping matrix A, thereby obtaining the spatial mapping relationship between the multiple sets of three-dimensional image data.

Here, in rigid body registration, the similarity between two sets of three-dimensional image data may be measured by minimum sum of absolute differences of pixel intensities, local gradients or local gray quotients, by minimum sum of squared differences of pixel intensities, local gradients or local gray quotients, by maximum cross-correlation of pixel intensities, local gradients or local gray quotients, or by minimum absolute difference of pixel intensities, local gradients or local gray quotients improved based on Rayleigh distribution characteristics of ultrasonic noise. One or more of the automatic registration methods between images described above may be selected through the prompt box, button, instruction input box or gesture provided by the mapping instruction receiving unit 122 to register the image data to obtain the spatial mapping relationship between the images.

Beside the automatic registration methods above, interactive registration methods involving manual selection may also be used. In the rigid body registration, the 3×3 matrix at upper left corner of the mapping matrix A may be a symmetric orthogonal matrix. A direct way for solving the rigid body registration between two sets of three-dimensional image data is selecting respectively in the two sets of three-dimensional image data four or more sets of point pairs and solving the optimum mapping matrix A using a least squares fitting method. The interactive registration method described above is a simple solution and there are many other methods for manually building a rigid mapping between two three-dimensional data which will not be described in detail herein. The interactive registration methods using manual selection of the present disclosure will also not be limited to those described above.

Figure 3:
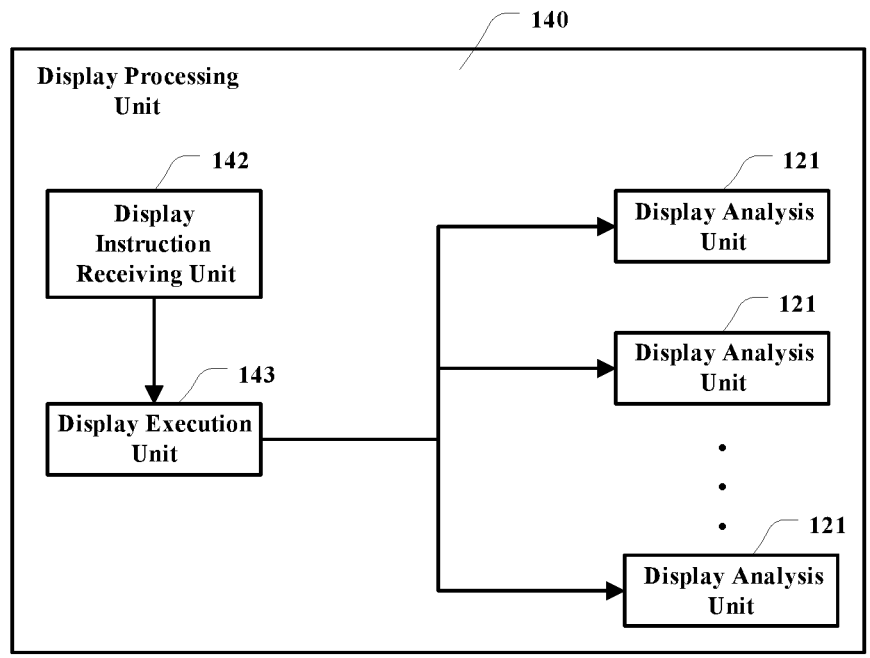
FIG. 3 schematically shows the display processing unit 140 in FIG. 1.

In one embodiment, as shown in FIG. 3, the display processing unit 140 may include:

at least two display analysis units 141. Each display analysis unit 141 may comparatively display the multiple displaying images obtained by reconstructing the multiple sets of three-dimensional image data in the display interface on the display device using one of the display methods below.

Figure 4:
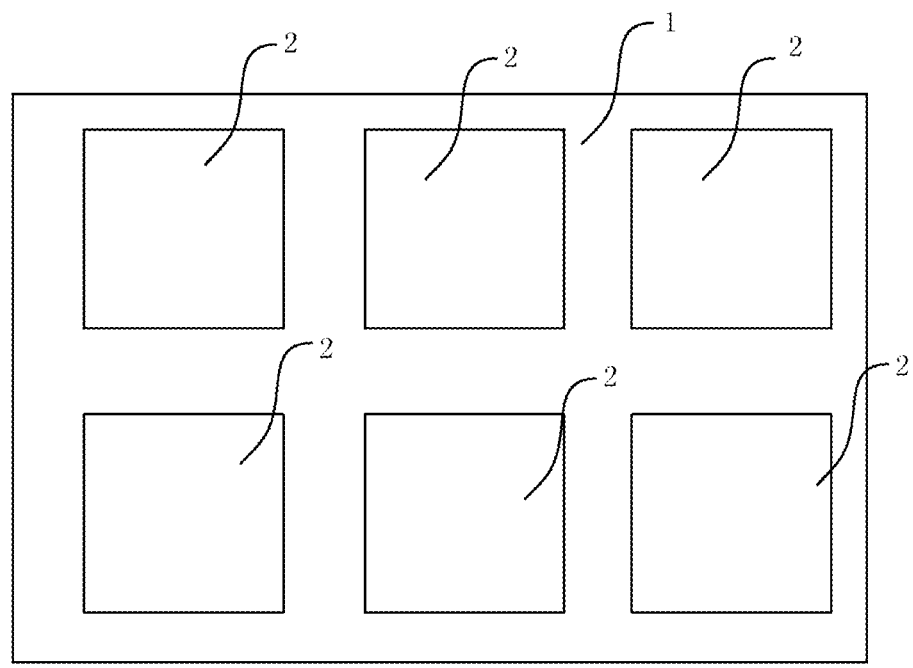
FIG. 4, FIG. 5 and FIG. 6 schematically show three comparative display methods.

The first display method may be as shown in FIG. 4. Multiple display regions 2 may be set in a same display interface 1 on the display device. In each display region, at least one displaying image (including two-dimensional image and/or three-dimensional image in at least one section reconstructed by multi-planar reconstruction) obtained by reconstructing one group of three-dimensional image data may be displayed. The displaying images of two sets of three-dimensional image data may be displayed side by side. For example, the displaying images of the three-dimensional image data before and after an operation may be displayed side by side. In this display method, when one display region or one pair of display regions are selected, the displaying image of the three-dimensional image data corresponding to said display region may be displayed in said display region or be enlarged in the display interface.

Figure 5:
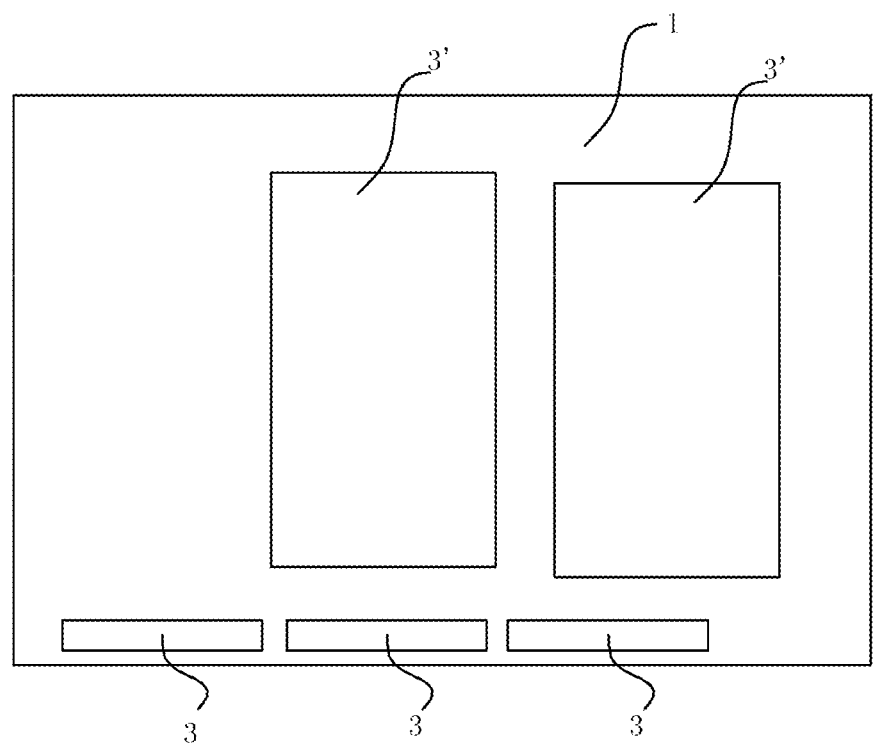

The second display method may be as shown in FIG. 5. Multiple display windows 3 may be set to respectively display multiple displaying images of each group of three-dimensional image data. When one display windows 3' is selected, the displaying image of the three-dimensional image data corresponding to said display window may be displayed in said display window or enlarged in the display interface. The display windows 3 here may be minimized to the lower portion of the display interface.

Figure 6:
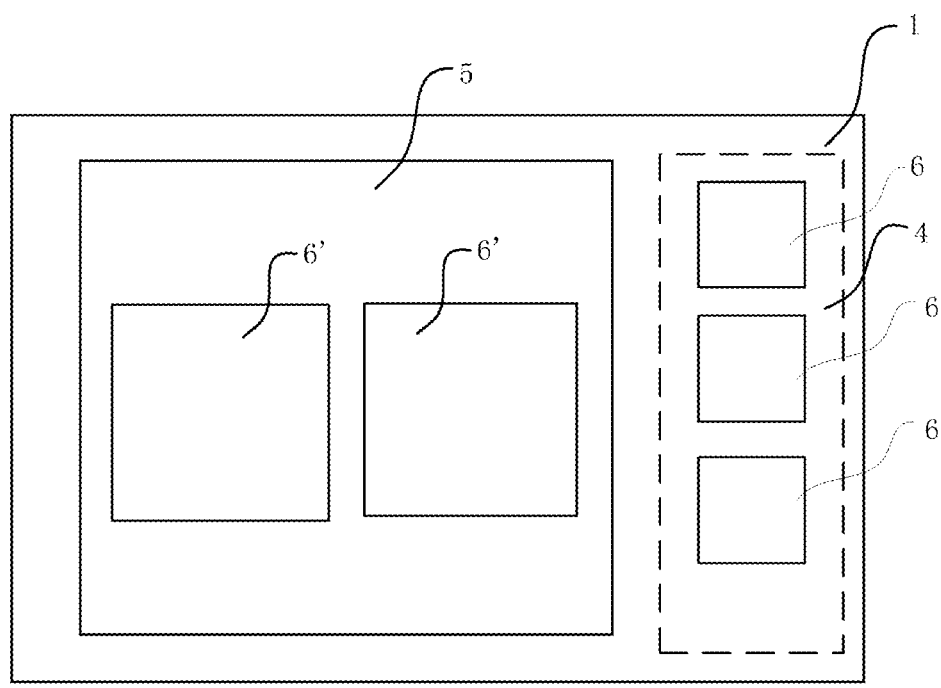

The third display method may be as shown in FIG. 6. A secondary display region 4 used for simultaneously displaying multiple sets of three-dimensional image data and a primary display region 5 used for displaying one or one pair of displaying images corresponding to the multiple sets of three-dimensional image data in an enlarged manner may be set in a same display interface 1. When any one or any one pair of displaying images 6 of the one or two sets of three-dimensional image data in the secondary display region are selected, the displaying image of the selected three-dimensional image data may be displayed (represented by 6') in the primary display region in an enlarged manner. Here, simultaneously displaying multiple sets of three-dimensional image data may include displaying multiple displaying images of the multiple sets of three-dimensional image data in the secondary display region in a scrollable manner The present disclosure will not be limited to the three display methods above. For example, a prompt box, button, instruction input box or gesture used for selecting at least one reconstruction section may be provided, thereby obtaining a reconstruction section selection instruction, and a two-dimensional image in the reconstruction section selected by the reconstruction section selection instruction may be reconstructed according to at least one of said other sets of three-dimensional image data. The two-dimensional image may be displayed on the display interface. For example, two-dimensional images in a same section of the reconstructed multiple sets of three-dimensional image data may be comparatively displayed. This way, only images in the same section may be provided in the display interface. Regarding the way for the comparison display, the methods of setting display regions, display windows or primary and secondary display region in the display interface on the display device described above may be referenced. Furthermore, regardless how the display regions are arranged and set in the display interface so as to display multiple displaying images obtained according to the reconstructed multiple sets of three-dimensional image data, all of the selected displaying images in the display interface may be marked, which may be used to generate display marks on the selected displaying images in the display interface or in the display regions used for displaying multiple displaying images corresponding to one sets of three-dimensional image data. Based on the display marks, the corresponding selected displaying images or display regions may be displayed in the display interface on the display device in an enlarged manner, or be comparatively/separately displayed in the display interface on the display device. The images displayed in an enlarged manner or displayed comparatively/separately here may include the displaying images on which the segmentation is not performed yet, and may also include the displaying images on which the segmentation has been performed and corresponding structural boundary of three-dimensional volume and safety boundary and regions thereof have been marked.

Therefore, the display processing unit may further display at least one displaying image obtained by reconstructing any one group of three-dimensional image data in the display interface, and the image marking unit may further mark the boundary described above and mark the area within the boundary on said at least one displaying image. Said at least one displaying image may be located in the same section with at least one displaying image obtained by reconstructing at least one group of three-dimensional image data of the other sets of three-dimensional image data.

As shown in FIG. 3, the display processing unit 140 may further include:

a display instruction receiving unit 142 which may provide a prompt box, a button, an instruction input box or a gesture used for selecting at least one display analysis unit above in the display interface 1 or the human-machine interaction input device so as to obtain a display selection instruction; and a display execution unit 143 which may call the selected display analysis unit based on the display selection instruction.

In the embodiment above, with the multiple display settings, more comparison display solutions may be provided to the user. The user of the ultrasonic image processing system 100 may select the desired comparison display solution based on needs or actual situations, such that the results of the image processing can be presented more intuitively.

Figure 7:
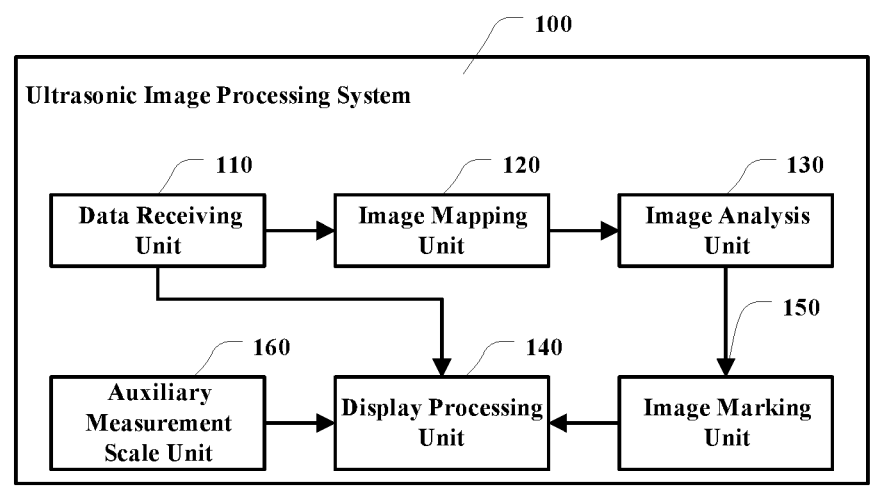
FIG. 7 schematically shows the ultrasonic image processing system in one embodiment.
Figure 8:
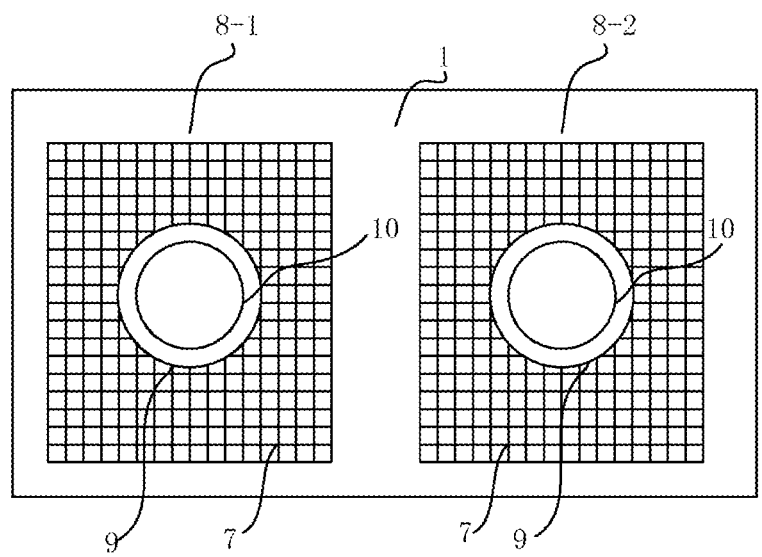
FIG. 8 schematically shows images on which the auxiliary measurement scales have been added.

In order to show the changes of situations of the disease area during the tumor ablation more intuitively, as shown in FIG. 7, the system 100 described above may further include an auxiliary measurement scale unit 160 which may superimpose an equal-pitch grid auxiliary measurement scale with a predetermined width on the displaying image so as to facilitate the position and the measurement. As shown in FIG. 8, the displaying images corresponding to two sets of three-dimensional image data may be displayed side by side in the display interface 1 on the display device. The three-dimensional image data before the operation may be displayed in the display region 8-1, while the three-dimensional image data after the operation may be displayed in the display region 8-2. The equal-pitch grid auxiliary measurement scales may be superimposed on the displaying images corresponding to the three-dimensional image data in the display regions 8-1 and 8-2. By performing segmentation on the three-dimensional image data before the operation to obtain the target area, the structural boundary 10 of three-dimensional volume and the safety boundary 9 may be obtained. The corresponding structural boundary 10 of three-dimensional volume and the safety boundary 9 in the three-dimensional image data after the operation may be accordingly obtained according to the mapping relationship. The boundaries may be displayed in the display regions 8-1 and 8-2. By superimposing the auxiliary measurement scale 7, the size of the three-dimensional volume of the target area and the distance to the safety boundary 9 may be shown more intuitively. In various embodiments, text information representing the predetermined width may further be superimposed on the auxiliary measurement scale so as to intuitively show the size of the three-dimensional volume of the target area and the distance to the safety boundary 9, thereby providing more direct judgment basis for the medical staffs such that they can make timely judgment.

In one embodiment, the pitch of the auxiliary measurement scale may be adjustable. In this case, the auxiliary measurement scale unit 160 may include:

a unit which may provide a prompt box, a button, an instruction input box or a gesture used for selecting a predetermined width in the display interface on the display device or on the human-machine interaction input device so as to obtain a width instruction;

a unit which may adjust the pitch of the equal-pitch grid auxiliary measurement scale according to the width instruction to obtain an adjusted equal-pitch grid auxiliary measurement scale; and a unit which may superimpose the adjusted equal-pitch grid auxiliary measurement scale on the displaying images.

Figure 9:
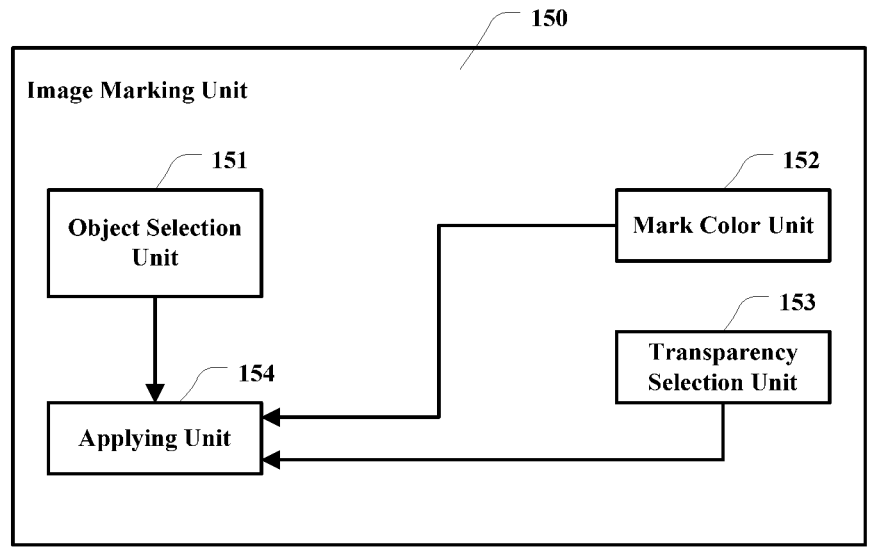
FIG. 9 schematically shows the image marking unit 150 in one embodiment.

In the embodiments above, the image marking unit 150 may use colors to mark the structural boundary of three-dimensional volume and the safety boundary in the displaying image. Alternatively, the image marking unit 150 may use different color transparencies to display the areas within the structural boundary of three-dimensional volume and the safety boundary in the displaying image. As shown in FIG. 9, specifically, the image marking unit 150 may include:

an object selection unit 151 which may obtain initial objects which will be marked and correspond to the structural boundary of three-dimensional volume or the safety boundary in the displaying image and/or initial objects which will be marked corresponding to the area located within the structural boundary of three-dimensional volume or the safety boundary. The initial objects corresponding to the structural boundary of three-dimensional volume or the safety boundary may be all pixels in a certain width in the vicinity of the boundary in the displaying image, and the initial objects corresponding to the area located within the structural boundary of three-dimensional volume or the safety boundary may be all pixels within the boundary or between the boundaries;

a mark color unit 152 which may provide a color prompt box, a button, an instruction input box or a gesture used for selecting a color in the display interface on the display device so as to obtain a color instruction;

a transparency selection unit 153 which may provide a prompt box, a button, an instruction input box or a gesture used for selecting a transparency in the area in the display interface so as to obtain a transparency instruction; and an applying unit 154 which may apply the color and/or transparency selected by the color instruction and/or the transparency instruction to the initial objects to be marked corresponding to the structural boundary of three-dimensional volume or the safety boundary and/or the area located within the structural boundary of three-dimensional volume or the safety boundary.

In various embodiments, more marking methods may be provided. The user of the ultrasonic image processing system 100 may select a desired marking method according to needs or actual situation such that the results of the image processing can be presented more intuitively.

Figure 10:
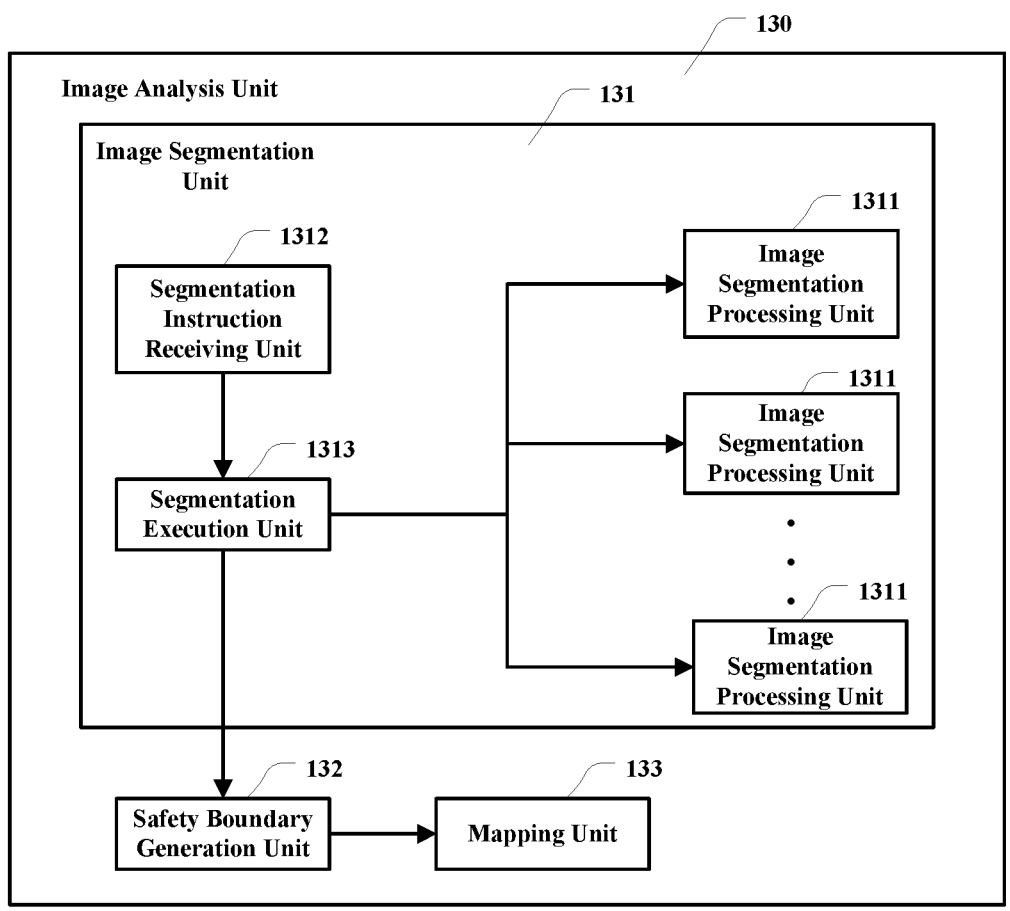
FIG. 10 schematically shows the image analysis unit 130 in one embodiment.

Based on the embodiments above, as shown in FIG. 10, the image analysis unit 130 may include:

an image segmentation unit 131 which may segment the target area according to any one group of three-dimensional image data of the three-dimensional image data above to obtain the boundary of the target area; and a mapping unit 133 which may map the boundary of the target area to other sets of three-dimensional image data with which the spatial mapping relationship has been obtained according to the spatial mapping relationship.

In the case that the boundary includes the structural boundary of three-dimensional volume and the safety boundary, the image analysis unit 130 may further include a safety boundary generation unit 132 which may expand outward or retract inward the structural boundary by a predetermined width to generate the safety boundary.

The image segmentation unit 131 may segment the target area from any one group of three-dimensional image data of the three-dimensional image data above to obtain the structural boundary of three-dimensional volume of the target area. Thereafter, the safety boundary generation unit 132 may expand outward or retract inward the structural boundary of three-dimensional volume by a predetermined width to generate the safety boundary. The mapping unit 133 may map the boundary of the target area to other sets of three-dimensional image data with which the spatial mapping relationship has been built according to the spatial mapping relationship.

The image segmentation unit 131 may further include:

at least one image segmentation processing unit 1311 each of which may segment the target area according to any one group of three-dimensional image data of the three-dimensional image data above using one image segmentation method;

a segmentation instruction receiving unit 1312 which may provide a prompt box, a button, an instruction input box or a gesture used for selecting at least one of the image segmentation unit above in the display interface on the display device or on the human-machine interaction input device so as to obtain a segmentation selection instruction; and a segmentation execution unit 1313 which may call the selected image segmentation unit according to the segmentation selection instruction.

In various embodiments, more image segmentation methods may be provided. The user of the ultrasonic image processing system 100 may select a desired image segmentation method according to need or actual situations such that the system may be more humane and the accuracy of the image processing may be increased.

In various embodiments, the image segmentation method may be Graph Cut method. For example, the tumor target area may be initially selected manually, thereafter an algorithm may be performed to automatically segment the tumor according to the difference between the gray distribution of the inside and outside of the tumor. Alternatively, an image segmentation method based on gray distribution may be used, in which it is assumed that an image include foreground parts and background parts and the gray distributions of the parts respectively satisfy Gaussian distribution. By defining an energy function based on variances of the gray distributions inside and outside the contour, the boundary of objects in the image may be solved. A manual segmentation may also be used. The contour of the tumor may be outlined manually in two-dimensional slices of the three-dimensional data, and the three-dimensional volume and shape of the tumor may be generated based on these two-dimensional contours. The image segmentation methods of the present disclosure will not be limited to those described above, and other methods may also be used. In the present disclosure, various image segmentation methods may be provide to the user for selection, but the specific image segmentation algorithm will not be limited. The segmentation for the target area may be performed after at least two three-dimensional ultrasound image collections are completed or after one group of three-dimensional image data is collected. For example, a first group of three-dimensional ultrasonic data may be collected and the target may be segmented therefrom, and after the tumor ablation is completed, a second group of three-dimensional ultrasonic data may be collected and registered with the first group. Based on the mapping obtained by the registration, the three-dimensional data and the results of the segmentation before and after the ablation operation may be comparatively displayed.

Based on the ultrasonic image processing system described above, as shown in FIG. 11, an ultrasonic image processing method may further be provided, which may include:

step 210: obtaining multiple three-dimensional image data of the same target tissue, where the multiple three-dimensional image data may include at least two sets of three-dimensional image data;

step 220: obtaining the spatial mapping relationship between the multiple sets of three-dimensional image data;

step 230: segmenting the target area based on any one group of three-dimensional image data of the multiple sets of three-dimensional image data above to obtain the boundary of the target area and mapping the boundary to other sets of three-dimensional image data with which the spatial mapping relationship has been obtained according to the spatial mapping relationship;

step 240: displaying, in the display interface, at least one displaying image obtained by reconstruction of at least one of said other sets three-dimensional image data;

step 250: marking the boundary or area with the boundary in the displaying image. The boundary here may include the structural boundary of three-dimensional volume and/or safety boundary. Regarding the meaning of the boundary and the area within the boundary, reference may be made to the related description above.

In one embodiment, the method may further include displaying, in the display interface, at least one displaying image obtained by reconstruction of any one group of three-dimensional image data and marking the boundary or the area within the boundary on the at least one displaying image, where the at least one displaying image obtained by the reconstruction of any one group of three-dimensional image data may be located at the same section with the at least one displaying image obtained by the reconstruction of at least one group of three-dimensional image data of the other sets of three-dimensional image data. For example, the multiple displaying images obtained by reconstructing the multiple sets of three-dimensional image data may be comparatively displayed in the display interface. The multiple displaying images here may include the two-dimensional images of a same section in the three-dimensional image reconstructed by MPR, and may also include the two-dimensional images in multiple sections in the reconstructed three-dimensional image and/or the three-dimensional image.

In one embodiment, the three-dimensional image data may be three-dimensional ultrasound tissue image data, three-dimensional ultrasound contrast image data, or three-dimensional image data containing both ultrasound tissue image data and three-dimensional ultrasound contrast image data.

In one embodiment, in order to provide more registration methods such that the user may select desired registration method according to need, the step 220 may include:

providing an prompt box, a button, an instruction input box or a gesture used for selecting at least one registration method in the display interface on the display device or on the human-machine interaction input device so as to obtain the mapping selection instruction; and calling the registration method selected by the mapping selection instruction to register the multiple sets of three-dimensional image data to obtain the spatial mapping relationship between the multiple sets of three-dimensional image data. Regarding the specific registration methods, reference may be made to the description about the mapping unit 120 above and they will not be described in detail here.

In one embodiment, in order to provide more comparative display methods such that the user can select desired display solutions according to needs, the step of comparatively displaying the multiple displaying images obtained by reconstructing the multiple sets of three-dimensional image data on the display device may include:

providing a prompt box, a button, an instruction input box or a gesture used for selecting a display method from the three display methods in the display interface on the display device or on the human-machine interaction device so as to obtain the display selection instruction, and calling the display method selected by the display selection instruction, where, regarding the three display methods, reference may be made to the description about the display processing unit 140 above.

Regarding the specific embodiments of the comparative display methods, reference may be made to the description related to FIG. 4, FIG. 5 and FIG. 6 above, and it will not be described here in detail again. The display methods listed herein are not exhaustive. In one embodiment, comparatively displaying the multiple displaying images obtained by reconstructing the multiple sets of three-dimensional image data in the display interface may be achieved by following steps. A prompt box, a button, an instruction input box or a gesture used for selecting at least one reconstruction section may be provided in the display interface on the display device or on the human-machine interaction input device so as to obtain the reconstruction section selection instruction. Thereafter, the two-dimensional image on the reconstruction section selected by the reconstruction section selection instruction may be reconstructed according to at least one group of three-dimensional image data of the other sets of three-dimensional image data, and may be displayed in the display interface. The reconstructed two-dimensional images of the multiple sets of three-dimensional image on the same section selected by the reconstruction section selection instruction may be comparatively displayed in the display interface. This method may facilitate the user to find the two-dimensional images which are desired to be display comparatively from a wide variety of image data and reduce the time for people to find the images.

In addition, in order to display the image or image area in an enlarged manner so as to facilitate the image segmentation or image view, the step of comparatively displaying the multiple displaying images obtained by reconstructing the multiple three-dimensional image data in the display interface may further include:

marking the selected displaying image or the display region used for displaying the multiple displaying images of one group of three-dimensional image data in the display interface (reference may be made to the description related to FIG. 4, FIG. 5 and FIG. 6 above, and the display region here may include the display areas and display windows in the figures) to obtain the display mark; and enlarging, or displaying, the selected displaying image or display region in the display interface according to the display mark.

Figure 12:
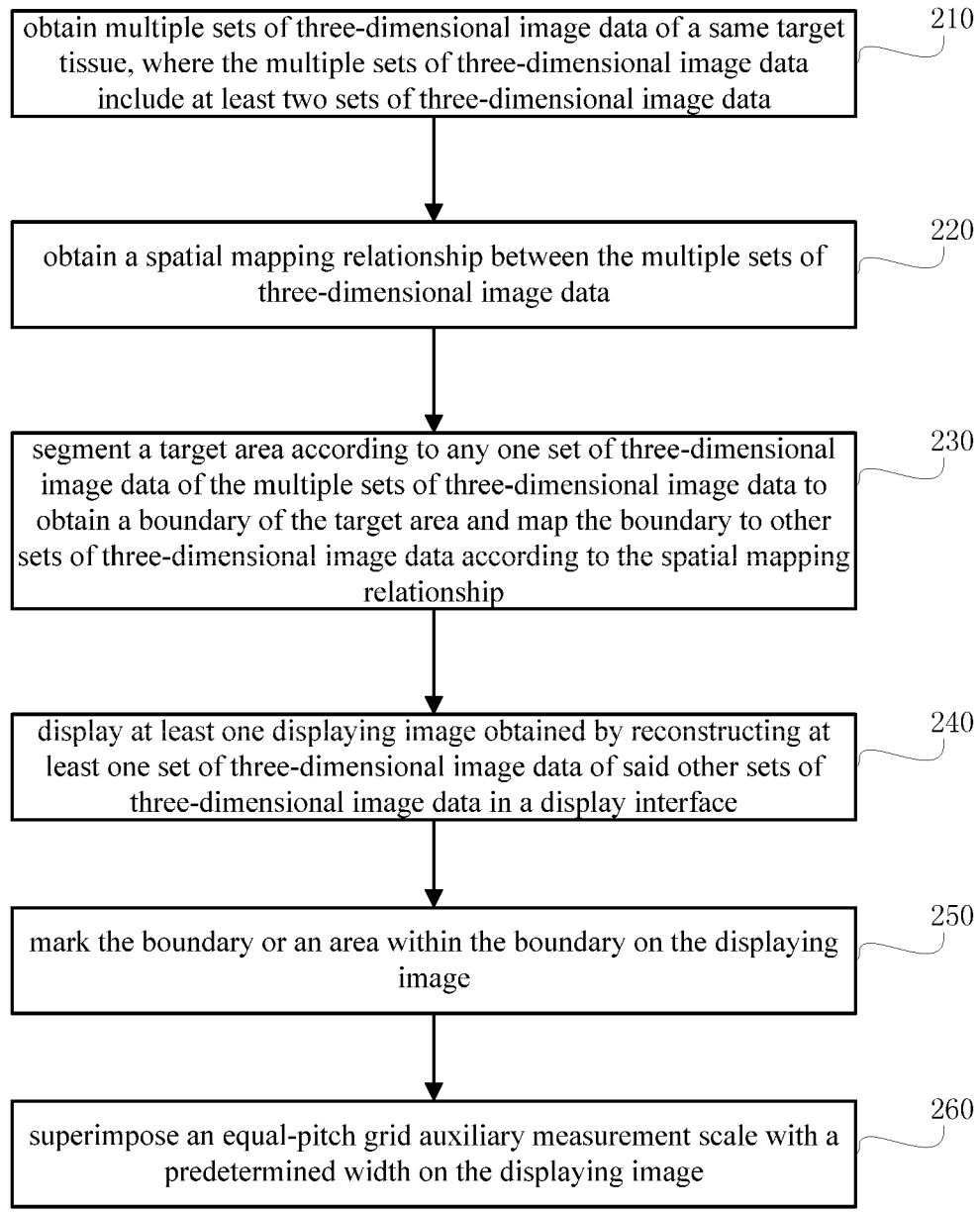
FIG. 12 is a flow chart of the ultrasonic image processing method in one embodiment.

In one embodiment, in order to show the changes of situation of the disease area during the tumor ablation treatment more intuitively, as shown in FIG. 12, the methods above may further include step 260: superimposing the equal-pitch grid auxiliary measurement scale with a predetermined width on the displaying image so as to facilitate the position and the measurement. In order to achieve that the pitch of the equal-pitch grid auxiliary measurement scale is adjustable, the step 260 may further include providing a prompt box, a button, an instruction input box or a gesture used for selecting a predetermined width in the display interface on the display device so as to obtain the width instruction, adjusting the pitch of the equal-pitch grid auxiliary measurement scale according to the width instruction to obtain adjusted equal-pitch grid auxiliary measurement scale, and superimposing the adjusted equal-pitch grid auxiliary measurement scale on the displaying image in the display interface. Regarding the effects of the equal-pitch grid auxiliary measurement scale, reference may be made to the description related to FIG. 7 and FIG. 8, which will not be described in detail here again.

In one embodiment, when performing the marking on the displaying image, colors may be used to mark the structural boundary of three-dimensional volume and the safety boundary on the displaying image, and/or different color transparency may be used to display the areas with in the structural boundary of three-dimensional volume and the safety boundary. In order to provide more marking methods such that the user can select desired marking method according to needs or actual situation, the marking step on the displaying image may include:

obtaining the structural boundary of three-dimensional volume or the safety boundary to be marked in the displaying image;

providing a color prompt box, a button, an instruction input box or a gesture used for selecting the color in the display interface on the display device or on the human-machine interaction input device so as to obtain the color instruction;

providing a prompt box, a button, an instruction input box or a gesture used for selecting the transparency in the area to be filled in the display interface on the display device or on the human-machine interaction input device so as to obtain the transparency instruction; and applying the color and/or transparency selected by the color instruction and/or the transparency instruction to the structural boundary of three-dimensional volume or the safety boundary and/or to the initial objects to be marked located in the area within the structural boundary of three-dimensional volume or the safety boundary.

In one embodiment, in order to provide more image segmentation methods such that the user can select desired image segmentation method according to needs, the step of segmenting the target area according to any one group of three-dimensional image data of the multiple sets of three-dimensional image data may include:

providing a prompt box, a button, an instruction input box or a gesture used for selecting at least one image segmentation method in the display interface or on the human-machine interaction input device so as to obtain the segmentation selection instruction; and calling the image segmentation method selected by the segmentation selection instruction to segment the target area from any one group of three-dimensional image data of the multiple sets of three-dimensional image data.

Regarding the specific details of the ultrasonic image processing method, reference may be made to the description related to the ultrasonic image processing system above. For example, regarding the image segmentation methods, reference may be made to the description related to the image segmentation unit 131.

Figure 11:
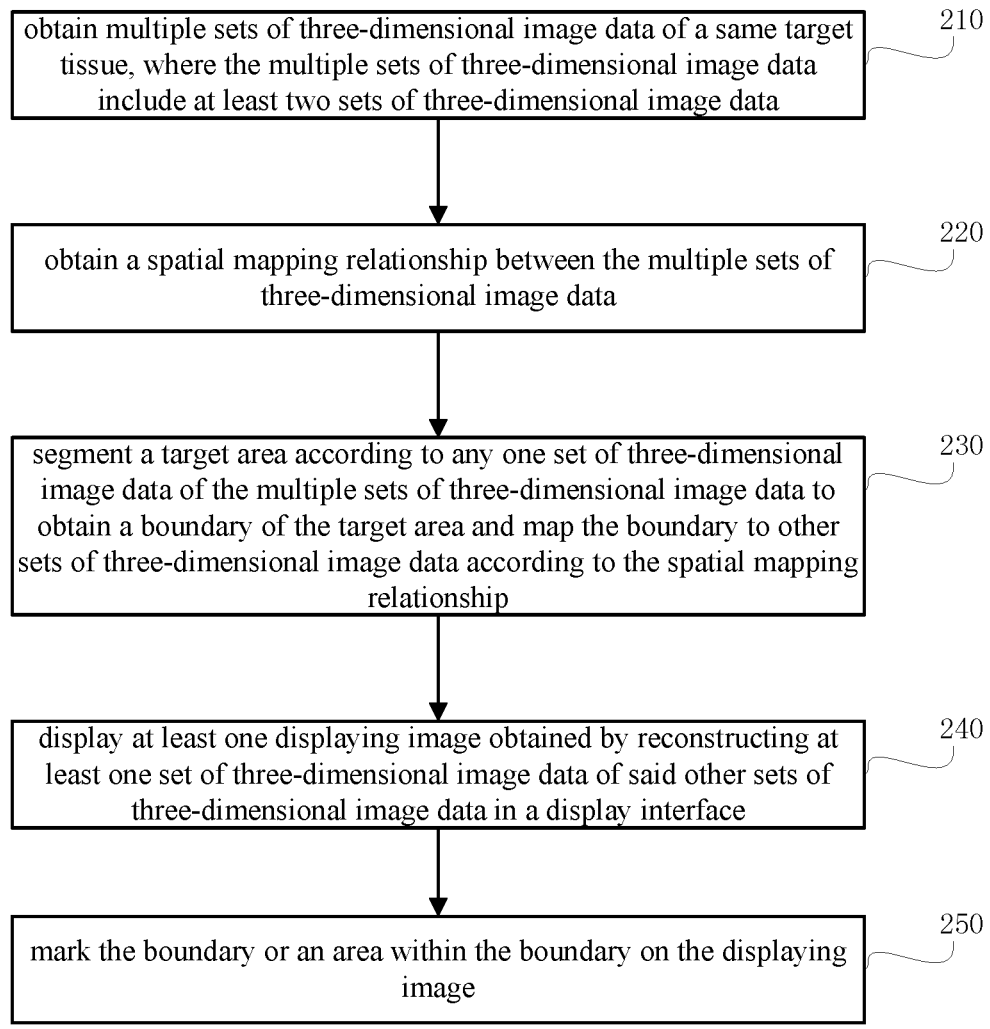
FIG. 11 is a flow chart of the ultrasonic image processing method in one embodiment.

FIG. 11 and FIG. 12 show the flow charts of the ultrasonic image processing methods of the present disclosure. It should be understood that although the steps are successively displayed according to the arrows in the flow charts of FIG. 11 and FIG. 12, these steps will not be performed necessarily according to the order indicated by the arrows. Unless explicitly stated, there will be no strict order in the performance of these steps. They may be performed in other orders. Furthermore, at least a portion of the steps in FIG. 11 and FIG. 12 may include multiple sub-steps or multiple stages, or additional steps or stages may further be added to those in FIG. 11 and FIG. 12 according to the description above. The sub-steps or stages will not be performed necessarily in the same time, but may be performed in different times. The sub-steps or stages will not be performed necessarily successively, but may be performed alternately with other steps or at least a portion of the sub-steps or stages of other steps.

By the description of the embodiments above, a person skilled in the art will understand that the methods in the embodiments above can be achieved by a universal hardware platform loaded with necessary software, or by hardware. Based on this understanding, the essential portion or contributing portion to existing technology of the ultrasonic image processing systems and methods of the present disclosure may be implemented by software products. The software products may be stored in a non-volatile computer readable storage medium (such as ROM, disk, CD or server storage device, etc.), and may include multiple instructions which may enable a terminal equipment (which may be a mobile phone, a computer, a server or a network equipment, etc.) to implement the systems and methods of the embodiments of the present disclosure.

Based on the systems and methods above, more personalized services may be provided to the user. The user can freely select the parameters and setting data in the image data processing and the image displaying. For example, in embodiments above, the prompt box, the button, the instruction input box or the gesture used for selecting the parameters or setting may be used so as to obtain the user manipulation data. However, the present disclosure will not be limited to these four ways. It should be understood as that various ways for selection, such as prompt box, button, instruction input box or gesture, etc. may be provided by the ultrasonic image processing device of the present disclosure so as to selecting manipulation data used for image segmentation, image registration or image display, etc. from pre-stored methods in the system, thereby providing more personalized, user-operable services to the user. The gesture here may include the touch operation on the display interface, sliding on the display interface or the like. Reference may be made to those provided by a mobile phone on its user interface.

Figure 13:
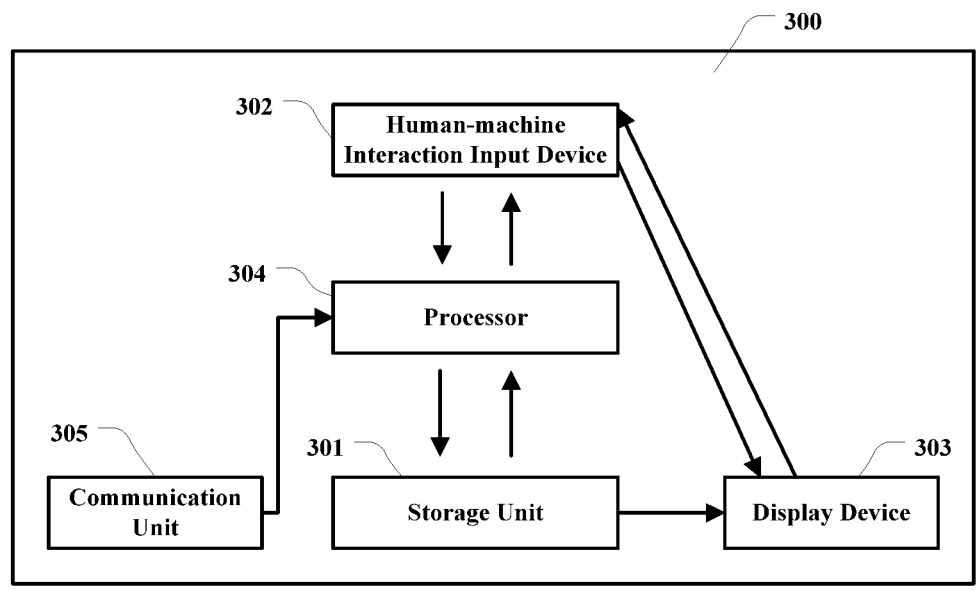
FIG. 13 schematically shows the ultrasonic image processing device in one embodiment.

The ultrasonic image processing systems and methods of the embodiments above may be applied to an ultrasonic image processing device such that the ultrasonic image processing device can quantitatively compare the effects of the tumor ablation. The multiple three-dimensional image data during the tumor ablation treatment may be effectively comparatively displayed, the changes of the situation of the disease area during the tumor ablation treatment can be shown intuitively in the display interface, and more effective quantitative data reference may be provided during medical procedures such as cancer treatment. Based on the description above, as shown in FIG. 13, in the present disclosure, an ultrasonic image processing device 300 may further be provided, which may include a storage unit 301 which may store obtained multiple sets of three-dimensional image data of the same target tissue, where the multiple sets of three-dimensional image data may include at least two sets of three-dimensional image data and the results of the manipulations performed on the three-dimensional image data, and the storage unit 301 may be a cache, a hard disk or the like;

a human-machine interaction input device 302 which may obtain the manipulation data to the multiple sets of three-dimensional image data, where the manipulation data may include inputting the three-dimensional image data, inputting the initial conditions for segmenting the target area and operation instructions for selecting the image segmentation method, the registration methods or the display methods, etc.;

a display device 303 which may display the displaying images obtained by reconstruction of the multiple sets of three-dimensional image data; and a processor 304 which may process the multiple sets of three-dimensional image data based on the received manipulation data and output the results of the processing to obtain the displaying image. The processor 304 may perform following steps when processing the multiple sets of three-dimensional image data:

obtaining the spatial mapping relationship between the multiple sets of three-dimensional image data, segmenting the target area according to any one group of three-dimensional image data of the multiple sets of three-dimensional image data to obtain the boundary of the target area, mapping the boundary to other sets of three-dimensional image data according to the spatial mapping relationship, obtaining at least one displaying image by reconstruction of at least one group of three-dimensional image data of said other sets of three-dimensional image data and displaying the at least one displaying image on the display device, and marking the boundary of the target area in the at least one displaying image or marking the area within the boundary on the at least one displaying image.

In one embodiment, in order to provide more comparative display methods such that the user can select desired comparative display method according to needs, the processor 304 may select one or more of the three display methods above to comparatively display the multiple displaying images obtained by reconstructing the multiple three-dimensional image data on the display device 303 according to the instruction obtained by the human-machine interaction input device 302. Regarding the specific solutions of the three display methods, reference may be made to the description related to FIG. 4, FIG. 5 and FIG. 6 above, which will not be described in detail here again.

Based on the three display methods in FIG. 4, FIG. 5 and FIG. 6, in order to find image data desired to be comparatively displayed from large amounts of image data, in one embodiment, a prompt box, a button, an instruction input box or a gesture used for selecting at least one reconstruction section may be provided in the display interface on the display device or in the human-machine interaction input device so as to obtain the reconstruction section selection instruction. The processor may reconstruct the two-dimensional image in the reconstruction section selected by the reconstruction section selection instruction according to at least one group of three-dimensional image data of said other sets of three-dimensional image data and display the two-dimensional image in the display interface. The displayed images may be the two-dimensional images in the same section of the multiple three-dimensional images. For example, in one embodiment, the processor may further:

obtain at least one displaying image by reconstructing any one group of three-dimensional image data and display the at least one displaying image in the display interface; and mark the boundary or the area within the boundary on said at least one displaying image;

where the at least one displaying image obtained by reconstructing said any one group of three-dimensional image data may be in the same section with the at least one display image obtained by reconstructing at least one group of three-dimensional image data of said other sets of three-dimensional image data.

Based on the three display methods in FIG. 4, FIG. 5 and FIG. 6, in order to facilitate the view and comparative display of important image, in one embodiment, the processor may mark the selected displaying image or the display region used for displaying the multiple displaying images of one group of three-dimensional image data in the display interface on the display device (reference may be made to the description related to FIG. 4, FIG. 5 and FIG. 6 above and the display region here may include the display areas and display windows in the figure) to generate the display mark, and enlarge, or display, the selected displaying image or display region in the display interface according to the display mark.

In one embodiment, when displaying the displaying images, the equal-pitch grid with the predetermined width may be superimposed on the displaying image as the background. Therefore, in one embodiment, the processor may provide a prompt box, a button, an instruction input box or a gesture used for selecting the predetermined width of the equal-pitch grid auxiliary measurement scale in the display interface on the display device or on the human-machine interaction input device such that the user can adjust the pitch of the equal-pitch grid in the display interface according to needs, thereby more intuitively showing the size of the three-dimensional volume of the target area and the distance from the safety boundary.

In one embodiment, colors may be used to mark the structural boundary of three-dimensional volume and the safety boundary on the displaying image, and/or different color transparencies may be used to mark the area located within the structural boundary of three-dimensional volume and the safety boundary on the displaying image.

In one embodiment, the device may further include a communication unit 305 which may obtain the multiple three-dimensional image data from Internet. In this embodiment, more three-dimensional image data related to the same target area may be obtained from a Internet sever to be comparatively displayed, thereby facilitating the understanding to the disease of the tissue and providing more, more intuitively comparative analysis of anatomical and physiological information for the study and diagnosis of the disease.

In one embodiment, the processor may provide a prompt box, a button, an instruction input box or a gesture used for selecting the registration methods between the images and/or the image segmentation methods in the display interface on the display device or on the human-machine interaction input device, and/or provide a prompt box, a button, an instruction input box or a gesture used for selecting the color and the transparency in the display interface on the display device or on the human-machine interaction input device. This way, compared with traditional ultrasonic image processing device, more personalized selection may be provided, thereby achieving comparative display of results of the processing with different algorithms and providing corresponding technical support for study and diagnosis of disease and the study on ultrasonic image processing. Regarding the specific details of the registration methods and the image segmentation methods, reference may be made to the description related to the mapping unit 120 and the image segmentation unit 131 above, which will not be described in detail here again.

In one embodiment, in order to determine whether the obtained three-dimensional image data belong to a same target tissue, the processor 304 may obtain labels of the multiple sets of three-dimensional image data and determine whether the multiple sets of three-dimensional image data belong to a same target tissue according to the labels. The multiple sets of three-dimensional image data of the same target tissue may be stored in the storage unit above with relevance. The content of the label may include a name of the part being scanned, scanning time and information which can uniquely determine an identity of a patient, etc. The information which can uniquely determine the identity of the patient may be ID card information or fingerprint information, etc.

Figure 14:
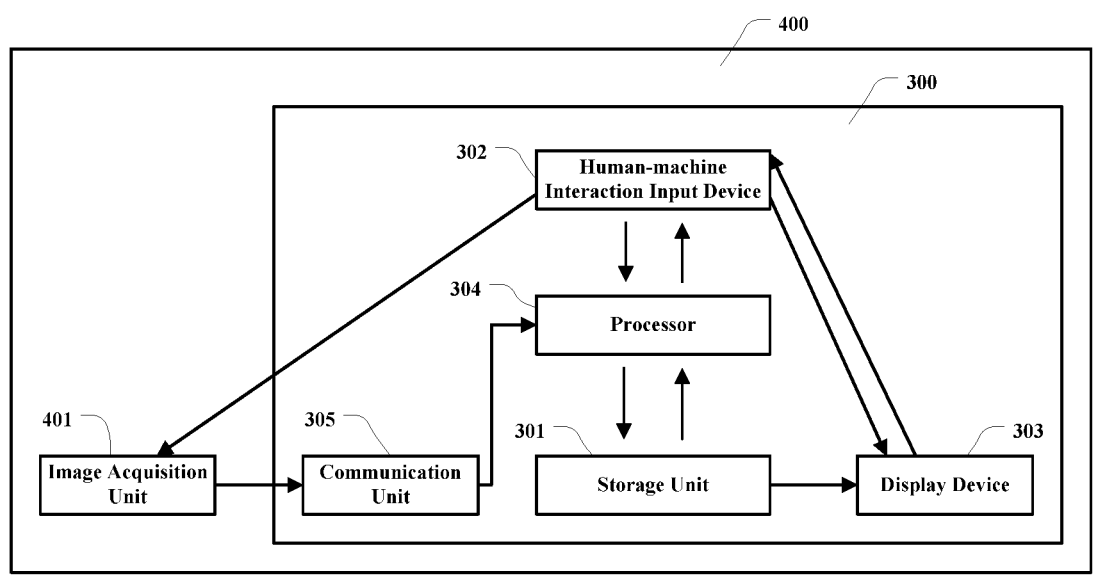
FIG. 14 schematically shows the ultrasonic diagnosis device in one embodiment.

Based on the ultrasonic image processing device, an ultrasonic diagnosis device 400 may also be provided, as shown in FIG. 14, which may include the ultrasonic image processing device 300 in the embodiments above and an image acquisition unit 401 which may transmit ultrasound waves and receive ultrasound echoes to obtain the three-dimensional image data of the target tissue.

The ultrasonic image processing device 300 may include: a storage unit 301 which may store the obtained multiple sets of three-dimensional image data of the same target tissue and the results of the operation performed on the multiple sets of three-dimensional image data, where the multiple sets of three-dimensional image data may include at least two sets of three-dimensional image data; a human-machine interaction input device 302 which may obtain the manipulation data to the multiple sets of three-dimensional image data; a display device 303 which may obtain the displaying image by reconstructing the multiple sets of three-dimensional image data; and a processor 304 which may process the multiple sets of three-dimensional image data according to the manipulation data and output the results of the processing. When processing the multiple sets of three-dimensional image data, the processor may obtain the spatial mapping relationship between the multiple sets of three-dimensional image data, segment the target area according to any one group of three-dimensional image data of the multiple sets of three-dimensional image data to obtain the boundary of the target area, map the boundary of the target area to other sets of three-dimensional image data according to the spatial mapping relationship, obtain at least one displaying image by reconstruction according to at least one group of three-dimensional image data of said other sets of three-dimensional image data and display the at least one displaying image on the display device, and mark the boundary of the target area or the area within the boundary on the at least one displaying image.

In one embodiment, the processor of the ultrasonic diagnosis device may further add labels to the three-dimensional image data acquired by the image acquisition unit 401. The labels may be used to distinguish the three-dimensional image data of different target tissues. The label here may include a name of the part being scanned, scanning time and information which can uniquely determine an identity of a patient, etc. The information which can uniquely determine the identity of the patient may be ID card information or fingerprint information, etc.

The image acquisition unit 401 in FIG. 13 and FIG. 14 may transmit ultrasound waves and receive ultrasound echoes, and process the ultrasound echoes to obtain the image data of the target tissue. The storage unit 301 may store the acquired image data, and may also store the data and parameters of other units generated during their operation. The processor 304 may automatically or semi-automatically process the images, such as perform the image registration, image segmentation, spatial mapping, multi planar reconstruction (MPR) or the like. The human-machine interaction input device 302 may manipulate the displayed image data in response to a keyboard, a mouse, a trackball or other hardware devices, such as trace the image, select the target or interactively register the image, etc. The display device 303 may display the acquired data and the results of the manipulation.

In general, the processor 304 may mainly process the image data, and may implement the functional units of the ultrasonic image processing systems above and perform the steps of the ultrasonic image processing methods above. Regarding the specific details of the ultrasonic image processing device 300, reference may be made to the related description above, which will not be described in detail here again.

An embodiment of the ultrasonic diagnosis device will be described below.

As shown in FIG. 14, first, the image acquisition unit 401 may acquire at least two sets of three-dimensional contrast data of the target area. For example, the image acquisition unit 401 may acquire the data respectively before and after the tumor ablation operation to obtain two sets of three-dimensional image data. During the acquisition, large acquisition angle and acquisition range may be used so as to obtain tissue data as rich as possible to facilitate the following image registration. A time interval may exist between the acquisitions of the two sets of three-dimensional ultrasound contrast data. During this time interval, other scanning or tumor ablation operation may be performed. The two data acquisitions may be performed respectively before and after the tumor ablation treatment. In clinical, generally the patient may have a rest on the bed for a while (more than half of one hour) after the tumor ablation treatment is completed. During this rest time, the gas generated in the vicinity of the tumor during the thermal ablation, which may affect the ultrasound imaging, may dissipate. The positions of the patient in the two acquisitions may be kept as consistent as possible, and the positions and directions of the probe in the two acquisitions before and after the operation may be kept as consistent as possible.

As shown in FIG. 13, the image data obtained in the acquisition may be processed by the ultrasonic image processing device 300. The label may be assigned to the image data acquired each time, and two sets of three-dimensional image data may be stored with relevance according to the contents of the labels.

The acquired two sets of three-dimensional image data of the same target tissue before and after the tumor ablation operation may be read from the storage unit 301, and the spatial mapping relationship between them may be obtained by image registration. The automatic registration methods may be used. For example, the mapping matrix A may be formed to build the spatial mapping relationship function between the two sets of three-dimensional ultrasonic images represented by the formula (1) above. Thereafter, the similarity measure function may be calculated based on minimum sum of absolute difference (SAD), as shown by the formula (2). The mapping matrix A may be solved based on the results of the similarity measure function, thereby obtaining the spatial mapping relationship between the multiple sets of three-dimensional image data.

Based on the spatial mapping relationship, the two sets of three-dimensional image data acquired before and after the tumor ablation operation may be comparatively displayed on the display device. The displayed images may be two-dimensional images which are in the section on which the tumor is located and are obtained according to MPR technology. The two-dimensional image in the section on which the tumor is located may be obtained by reconstructing the three-dimensional image data before the operation and be displayed on the display region 8-1 in the display interface 1 on the display device, as shown in FIG. 8. The two-dimensional image in the same section with the two-dimensional image obtained according to the three-dimensional image data before the operation may be obtained by reconstructing the three-dimensional image data after the operation and displayed on the display region 8-2 in FIG. 8. When displaying the two-dimensional images, the equal-pitch grid 7 may be additionally displayed as background.

The image segmentation may be performed on the two-dimensional image of the three-dimensional image data before the operation displayed on the display region 8-1 to extract the target area (such as the tumor tissue), thereby obtaining the structural boundary 10 of three-dimensional volume of the tumor tissue. The structural boundary 10 of three-dimensional volume may be expended outward by 5 mm in the binary image using a morphological dilation to obtain the safety boundary 9. The obtained structural boundary 10 of three-dimensional volume and the safety boundary 9 may be mapped to the three-dimensional image data after the operation according to the solved spatial mapping relationship. The structural boundary of three-dimensional volume and the safety boundary, or the area within the structural boundary of three-dimensional volume and the safety boundary, may be marked on the two-dimensional images which may be obtained by reconstructing the three-dimensional image data before and after the operation and be displayed respectively on the display region 8-1 and the display region 8-2.

The color and/or transparency used in the marking operation above may be selected through the prompt box provided in the display interface. Different colors may be used to mark the structural boundary 10 of three-dimensional volume and the safety boundary 9 on the two-dimensional images displayed in the display region 8-1 and the display region 8-2. Different transparencies may be used to mark the areas within the structural boundary 10 of three-dimensional volume and the safety boundary 9 on the two-dimensional images displayed in the display region 8-1 and the display region 8-2.

This way, the three-dimensional images before and after the operation, and the sizes of the three-dimensional volume of the tumor tissue and the safety boundaries before and after the operation, may be simultaneously displayed in the display interface on the display device. The treatment effects of the tumor ablation may be quantitatively displayed, and a basis for quantitative judgment whether the tumor ablation treatment is effectively applied may be provided to the medical staffs.

The image processing systems, methods and devices and the diagnosis device using the same may be used to evaluate the effects of the ablation treatment to liver tumor. Furthermore, they may also be used to evaluate the effects of minimally invasive intervention treatment to human tissue such as uterus or prostate, etc. The image processing systems, methods and devices and the diagnosis device using the same of the present disclosure may provide technologies for evaluating and displaying the effects of tumor ablation treatment which can quantitatively comparatively analyze the relative positional relationship between the tumor tissue and the safety boundary and the ablated area and show the size of the area with insufficient ablation intuitively and quantitatively. In the present disclosure, three-dimensional ultrasound contrast imaging technologies may be used to imaging the target area of the tumor at least two times, i.e. at least before and after the operation, to obtain at least two sets of data of the target area before and after the operation.

The three-dimensional volume and shape of the target area may be segmented according to one group of data. The correspondence between the two sets of data may be obtained using image registration or other technologies. Based on the mapping relationship between the two sets of data, the three-dimensional shape of the target area obtained according to one group of data may be mapped to the other group of data. The states of the target area may be comparatively displayed in multiple windows (or multiple display regions). For example, the two-dimensional images of one group of data obtained by MPR (multi-planar reconstruction) and the intersection areas of the three-dimensional volume and shape of the target area with said two-dimensional images may be displayed in one window (or display region), while, based on the correspondence between the two sets of data, the two-dimensional images reconstructed using the other group of data which correspond to said one window (or display region) and the intersection areas of the three-dimensional volume and shape of the target area with the two-dimensional images may be displayed in the other window (or display region). Furthermore, based on the mapping relationship between the two sets of data obtained by registration, the operations performed on one window (or display region), such as measurement, trace or segmentation, etc, may be mapped to the other window (or display region), thereby intuitively comparing the two sets of three-dimensional image data to evaluate the effects of the tumor ablation treatment. Therefore, visible quantitative data may be provided to the medical staffs to determine on-site whether the ablated area has covered the whole tumor tissue area.

Several embodiments have been described above. The description is specific and detailed. However, the description above should not be interpreted as limitations to the present disclosure. Many modifications and improvements may be made by a person ordinarily skilled in the art without departing from the concepts of the present disclosure, which all belong to the scope of protection of the present disclosure. Therefore, the protection scope of the present disclosure shall be defined by the claims below.

We claim:

1. An ultrasonic image processing system, comprising:
a processor; and
a non-volatile computer readable storage medium storing multiple instructions that, when executed by the processor, cause the processor to:
obtain multiple sets of three-dimensional image data of a same target tissue, wherein the multiple sets of three-dimensional image data comprises at least two sets of three-dimensional image data;
obtain a spatial mapping relationship between the multiple sets of three-dimensional image data;
segment a target area according to any one group of three-dimensional image data of the multiple sets of three-dimensional image data to obtain a boundary of the target area and maps the boundary to other sets of three-dimensional image data according to the spatial mapping relationship;
display at least one displaying image obtained by reconstructing at least one group of three-dimensional image data of said other sets of three-dimensional image data in a display interface; and
mark the boundary or an area within the boundary on the displaying image;
wherein, when obtaining a spatial mapping relationship between the multiple sets of three-dimensional image data, the processor is configured to:
obtain a mapping selection instruction for selecting at least one of the registration method through a prompt box, a button, an instruction input box or a gesture; and
obtain the spatial mapping relationship between the multiple sets of three-dimensional image data using a registration method selected by the mapping selection instruction.

2. The ultrasonic image processing system of claim 1, wherein the processor is configured to obtain reconstruction section selection instruction through a prompt box, a button, an instruction input box or a gesture used for selecting at least one reconstruction section, reconstructs a two-dimensional image in a reconstruction section-selected by the reconstruction section selection instruction according to at least one group of three-dimensional image data of said other sets of three-dimensional image data, and displays the two-dimensional image in the display interface.

3. The ultrasonic image processing system of claim 1,
wherein the processor is further configured to superimpose an equal-pitch grid auxiliary measurement scale with a predetermined width on the displaying image.

4. The ultrasonic image processing system of claim 3, wherein the processor is configured to:
obtain a width instruction through a prompt box, a button, an instruction input box or a gesture used for selecting the predetermined width;
adjust a pitch of the equal-pitch grid auxiliary measurement scale according to the width instruction to obtain an adjusted equal-pitch grid auxiliary measurement scale; and
superimpose the adjusted equal-pitch grid auxiliary measurement scale on the displaying image.

5. The ultrasonic image processing system of claim 1, wherein the processor is configured to mark the boundary on the displaying image with colors and/or marks the area within the boundary on the displaying image with different transparency.

6. The ultrasonic image processing system of claim 1, wherein the processor is configured to:
segment the target area according to any one group of three-dimensional image data of the multiple sets of three-dimensional image data to obtain the boundary of the target area; and
map the boundary of the target area to other sets of three-dimensional image data with which the spatial mapping relationship has been obtained according to the spatial mapping relationship.

7. The ultrasonic image processing system of claim 6, wherein the processor is configured to:
obtain a segmentation selection instruction through a prompt box, a button, an instruction input box or a gesture used for selecting at least one image segmentation method; and
segment the target area according to any one group of three-dimensional image data of the multiple sets of three-dimensional image data using an image segmentation method selected by the segmentation selection instruction.

8. The ultrasonic image processing system of claim 1, wherein, the processor is further configured to display at least one displaying image obtained by reconstructing said any one group of three-dimensional image data in the display interface and mark the boundary or the area within the boundary on the at least one displaying image obtained by reconstructing said any one group of three-dimensional image data, wherein the at least one displaying image obtained by reconstructing said any one group of three-dimensional image data is in a same section with the at least one displaying image obtained by reconstructing any one group of three-dimensional image data of said other sets of three-dimensional image data.

9. The ultrasonic image processing system of claim 1, wherein the boundary is a structural boundary of three-dimensional volume of the target area and/or a safety boundary generated by expanding outward or retracting inward a structural boundary of three-dimensional volume of the target area.

10. An ultrasonic image processing method, comprising:
obtaining multiple sets of three-dimensional image data of a same target tissue, wherein the multiple sets of three-dimensional image data comprises at least two sets of three-dimensional image data;
obtaining a spatial mapping relationship between the multiple sets of three-dimensional image data;
segmenting a target area according to any one group of three-dimensional image data of the multiple sets of three-dimensional image data to obtain a boundary of the target area and mapping the boundary to other sets of three-dimensional image data according to the spatial mapping relationship;
displaying at least one displaying image obtained by reconstructing at least one group of three-dimensional image data of said other sets of three-dimensional image data in a display interface; and
marking the boundary or an area within the boundary on the displaying image;
wherein obtaining the spatial mapping relationship between the multiple sets of three-dimensional image data comprises:
obtaining a mapping selection instruction for selecting at least one registration method through a prompt box, a button, an instruction input box or a gesture; and
obtaining the spatial mapping relationship between the multiple sets of three-dimensional image data using a registration method selected by the mapping selection instruction.

11. The ultrasonic image processing method of claim 10, wherein displaying at least one displaying image obtained by reconstructing at least one group of three-dimensional image data of said other sets of three-dimensional image data in a display interface comprises:
obtaining a reconstruction section selection instruction through a prompt box, a button, an instruction input box or a gesture used for selecting at least one reconstruction section; and
reconstructing a two-dimensional image in a reconstruction section selected by the reconstruction section selection instruction according to at least one group of three-dimensional image data of said other sets of three-dimensional image data, and displaying the two-dimensional image in the display interface.

12. The ultrasonic image processing method of claim 10, wherein displaying at least one displaying image obtained by reconstructing at least one group of three-dimensional image data of said other sets of three-dimensional image data in a display interface comprises:
marking a selected displaying image in the display interface or a selected display region in which multiple displaying images of one group of three-dimensional image data are displayed to generate a display mark;
enlarging or displaying the selected display image or the selected display region in the display interface.

13. The ultrasonic image processing method of claim 10, further comprising superimposing an equal-pitch grid auxiliary measurement scale with a predetermined width on the displaying image.

14. The ultrasonic image processing method of claim 13, further comprising:
obtaining a width instruction through a prompt box, a button, an instruction input box or a gesture used for selecting the predetermined width;
adjusting a pitch of the equal-pitch grid auxiliary measurement scale according to the width instruction to obtain an adjusted equal-pitch grid auxiliary measurement scale;
and
superimposing the adjusted equal-pitch grid auxiliary measurement scale on the displaying image.

15. The ultrasonic image processing method of claim 10, wherein segmenting the target area according to any one group of three-dimensional image data of the multiple sets of three-dimensional image data comprises:
obtaining a segmentation selection instruction through a prompt box, a button, an instruction input box or a gesture used for selecting at least one image segmentation method; and
segmenting the target area according to any one group of three-dimensional image data of the multiple sets of three-dimensional image data using an image segmentation method selected by the segmentation selection instruction.

16. The ultrasonic image processing method of claim 10, further comprising:
displaying at least one displaying image obtained by reconstructing said any one group of three-dimensional image data in the display interface; and
marking the boundary or the area within the boundary on the at least one displaying image obtained by reconstructing said any one group of three-dimensional image data;
wherein the at least one displaying image obtained by reconstructing said any one group of three-dimensional image data is in a same section with the at least one displaying image obtained by reconstructing any one group of three-dimensional image data of said other sets of three-dimensional image data.

17. The ultrasonic image processing system of claim 10, wherein the boundary is a structural boundary of three-dimensional volume of the target area and/or a safety boundary generated by expanding outward or retracting inward a structural boundary of three-dimensional volume of the target area.

18. An ultrasonic diagnosis device, comprising:
a probe configured to transmit ultrasound waves and receives ultrasound echoes to obtain three-dimensional image data of a target tissue; and
an ultrasonic image processing device comprising:
a non-volatile computer readable storage medium which stores multiple sets of three-dimensional image data of a same target tissue and results of manipulations performed on the multiple sets of three-dimensional image data, wherein the multiple sets of three-dimensional image data comprises at least two sets of three-dimensional image data;
a human-machine interaction input device which obtains manipulation data to the multiple sets of three-dimensional image data;

a display device which displays the displaying image obtained by reconstruction of the multiple sets of three-dimensional image data; and a processor which processes the multiple sets of three-dimensional image data based on the obtained manipulation data and outputs results of the processing, wherein the processor is configured to:

obtain a spatial mapping relationship between the multiple sets of three-dimensional image data;

segment a target area according to any one group of three-dimensional image data of the multiple sets of three-dimensional image data to obtain a boundary of the target area, and maps the boundary of the target area to other sets of three-dimensional image data according to the spatial mapping relationship;

obtain at least one displaying image by reconstruction of at least one group of three-dimensional image data of said other sets of three-dimensional image data and displays the at least one displaying image on the display device; and mark the boundary of the target area on the at least one displaying image or marks an area within the boundary on the at least one displaying image;

wherein, when obtaining a spatial mapping relationship between the multiple sets of three-dimensional image data, the processor is configured to:

obtain a mapping selection instruction for selecting at least one of the registration method through a prompt box, a button, an instruction input box or a gesture; and obtain the spatial mapping relationship between the multiple sets of three-dimensional image data using a registration method selected by the mapping selection instruction.

\* \* \* \* \*